(12) United States Patent
Rouhani et al.

(10) Patent No.: US 6,770,451 B2
(45) Date of Patent: Aug. 3, 2004

(54) SCREENING FOR ENZYME INHIBITORS

(75) Inventors: Riaz Rouhani, Concord, CA (US); Inna Vainshtein, Palo Alto, CA (US)

(73) Assignee: Discoverx, Inc., Fremont, CA (US)

( * ) Notice: Subject to any disclaimer, the term of this patent is extended or adjusted under 35 U.S.C. 154(b) by 195 days.

(21) Appl. No.: 10/137,952

(22) Filed: May 3, 2002

(65) Prior Publication Data

US 2003/0170765 A1 Sep. 11, 2003

Related U.S. Application Data

(60) Provisional application No. 60/289,911, filed on May 9, 2001, and provisional application No. 60/357,355, filed on Feb. 15, 2002.

(51) Int. Cl.[7] .............................. C12Q 1/48; C12Q 1/34; C12Q 1/42; C12Q 1/26; C12Q 1/54
(52) U.S. Cl. .............................. 435/15; 435/18; 435/21; 435/25; 435/14
(58) Field of Search .............................. 435/15, 18, 21, 435/25, 14

(56) References Cited

U.S. PATENT DOCUMENTS

2003/0170765 A1 * 9/2003 Rouhani et al. ............ 435/7.92

OTHER PUBLICATIONS

Sasaki et al, Biochem and Biophy Research Communications, V214(3(, pp 1114–1120, (Sep. 25, 1995) (Abstract Only).*

* cited by examiner

Primary Examiner—Louise N. Leary
(74) Attorney, Agent, or Firm—Bertram Rowland

(57) ABSTRACT

Systems, including methods and reagents, for identifying enzyme inhibitors. The systems employ a conjugate of a known inhibitor of a target enzyme and an enzyme donor, an enzyme acceptor that binds to the enzyme donor to form an active indicator-enzyme complex, and a detectable substrate for the indicator enzyme. The assay is performed by combining the candidate agent, the conjugate of the known inhibitor and enzyme donor, the enzyme acceptor, and the substrate under binding conditions, where the candidate compound competes with the conjugate for the target enzyme. By measuring the rate of product formation or substrate depletion catalyzed by the indicator enzyme, the inhibitory activity of the candidate compound can be determined. The methodology is particularly applicable for target enzymes that have substrates or products that are difficult to synthesize and/or detect, such as kinases and phosphatases.

51 Claims, 2 Drawing Sheets

SCREENING FOR ENZYME INHIBITORS

CROSS-REFERENCES

This application is based on and claims priority of the U.S. Provisional Patent Application Serial No. 60/289,911, filed May 9, 2001, and claims benefit of 60/357,355 filed Feb. 15, 2002, entitled SCREENING FOR ENZYME INHIBITORS.

BACKGROUND OF THE INVENTION

1. Field of the Invention

The invention relates to screening assays. More specifically, the invention relates to screening assays for enzyme inhibitors using enzyme complementation.

2. Background and Related Disclosures

The impending resolution of the human and other genomes has provided an extensive repertoire of protein targets for modulation of mammalian physiology. The ability to identify the genes of the mammalian genomes has greatly expanded the need to determine the function of the proteins and the manner in which proteins interact to fulfill their function. At the same time, combinatorial approaches have greatly expanded the number of candidate compounds that may serve as drugs. Due to the large number of permutations and combinations, there is a particular need for rapid, accurate assays that do not require numerous steps, complicated protocols, and expensive reagents and equipment for their performance.

There is a rich literature of protocols and reagents for performing analyte determinations. For the most part, with haptens that are monoepitopic and frequently with antigens that are polyepitopic, competitive assays are employed. That is, the analyte and a modified analyte compete for a binding protein. Binding of the modified analyte with the binding protein results in signal modulation, where the modulation is related to the amount of analyte present in the sample.

For the most part, the binding protein has been polyclonal or monoclonal antibodies. These binding proteins are preferred because of their high affinity and specificity. In addition, the off-rate of the analyte or modified analyte is relatively slow, with the equilibrium under the conditions of the assay being driven toward the binding complex, rather than toward the unbound analyte. The success of the assay has been dependent on obtaining an extended dynamic range and clean results due to the high binding affinity of the antibodies.

Where one is interested in determining the binding of an agent to a target, various protocols may be employed. Where the target has a lower affinity than an antibody, protocols requiring an antibody in competition with the target will generally not be useful. Since the binding of the agent is reversible, the agent would distribute itself between the antibody and the target. Unless the target and the antibody have comparable binding affinities, the agent would primarily bind to the one that has the higher binding affinity, providing a very small dynamic range.

Alternatively, one may provide a modified agent, where the agent is coupled to a detectable label, and allow for a competition between the modified agent and the agent for the target. One may then isolate the complex of the target with the modified agent and detect the level of binding to the target, which can be correlated to the binding affinity of the agent to the target. This requires that a different modified agent must be prepared for each agent.

In particular for enzyme inhibitor assays, one approach has been to develop antibodies to the product and monitor the formation of product in the presence of an inhibitor. This approach is exemplified by kinases and phosphatases, where antibodies are made that are specific for a phosphorylated or dephosphorylated product. This approach requires that a different substrate be prepared for each enzyme and different antibodies be prepared for each product. In fact, the preparation of antibodies to the phosphorylated or dephosphorylated product that distinguish between the product and the much greater amount of substrate has proven problematical.

Previous studies have shown that [$^3$H]-staurosporine (Herbert et al, *BBRC*, 171, 189–195 (1990)) as well as [$^3$H]-dimethylstaurosporine (Gross et al, *Biochem. Pharmacol.*, July 15;40(2):343–50 (1990)) bind reversibly to PKC-alpha.

The following U.S. Pat. No. 4,378,428, issued Mar. 29, 1983; U.S. Pat. No. 4,708,929, issued Nov. 24, 1987; U.S. Pat. No. 5,037,735, issued Aug. 6, 1991; U.S. Pat. No. 5,106,950, issued Apr. 21, 1992; U.S. Pat. No. 5,362,625, issued Nov. 8, 1994; U.S. Pat. No. 5,464,747, issued Nov. 7, 1995; U.S. Pat. No. 5,604,091, issued Feb. 18, 1997; U.S. Pat. No. 5,643,734, issued Jul. 1, 1997; U.S. Pat. No. 6,270,964, issued Aug. 7, 2001; and U.S. Pat. No. 6,294,330, issued Sep. 25, 2001 describe related subject matter. Applications WO 96/19732 and WO 98/06648 describe assays using complementation of enzyme fragments, and WO 00/072011 and WO 98/09169 describe assays for kinases and phosphatases. All patents, patent applications and references cited herein are hereby incorporated by reference in their entirety.

None of the above references provide methods and protocols for rapid screening of a large number of different agents to determine the affinity of the agents for a particular target.

It is, therefore, a subject of this invention to provide such method and protocols which permits rapid screening of a large number of different agents for their affinity to bind to a particular target.

SUMMARY OF THE INVENTION

The invention provides systems, including methods and reagents, for identifying enzyme inhibitors. The systems employ a conjugate of an enzyme donor and a known inhibitor of a target enzyme, an enzyme acceptor that binds to the enzyme donor to form an active indicator-enzyme complex, and a substrate for the indicator enzyme. The assay is performed by combining a candidate inhibitor compound, the conjugate of the enzyme donor and known inhibitor, the enzyme acceptor, and the substrate under binding conditions, where the candidate compound competes with the conjugate for the target enzyme. By measuring the rate of product formation or substrate depletion catalyzed by the indicator enzyme, the inhibitory activity of the candidate compound can be determined. The methodology may be particularly applicable for target enzymes that have substrates or products that are difficult to synthesize and/or detect, such as kinases and phosphatases.

DETAILED DESCRIPTION OF THE INVENTION

Figure 1:
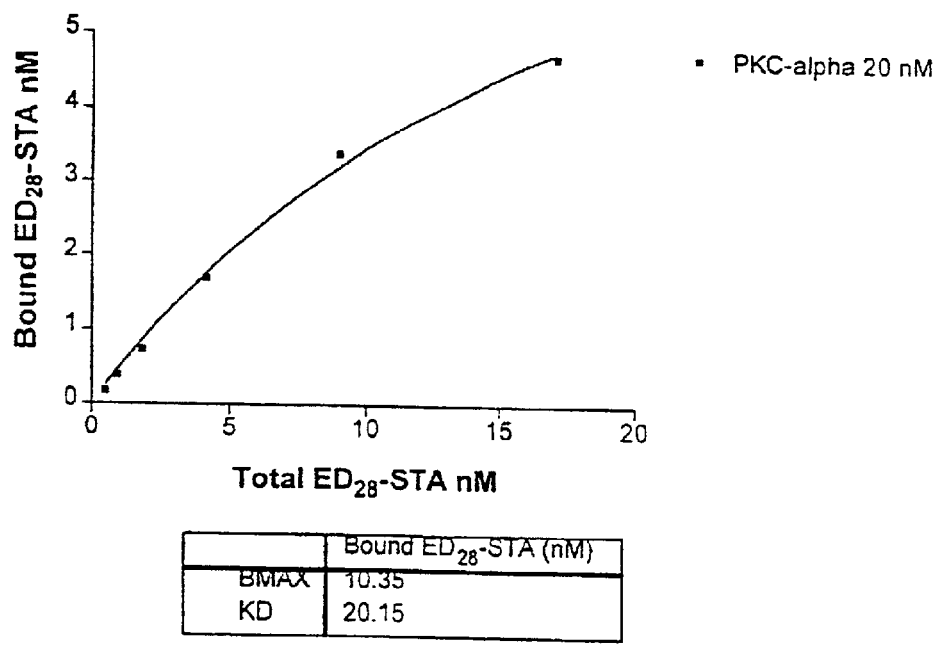
FIG. 1 is a graph of the binding of staurosporine labeled with $ED_{28}$ ($ED_{28}$-STA derivative) to PKC-alpha.
Figure 2:
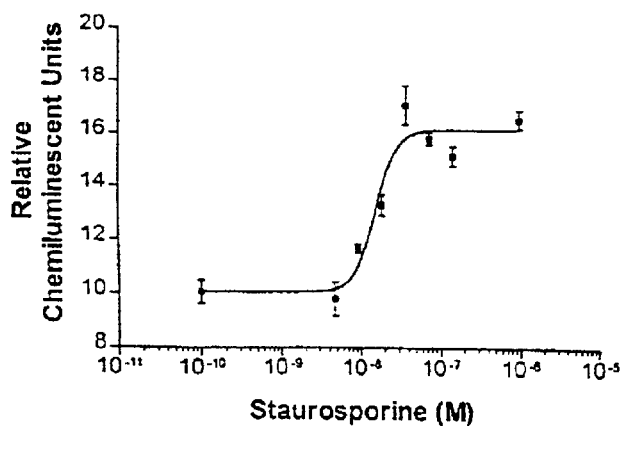
FIG. 2 is a graph of the competitive binding of staurosporine and ED28-STA to PKC-alpha.

The subject methodologies and compositions are concerned with screening, particularly high-throughput screening, for biologically active agents modulating the activity of target proteins.

In particular, the subject invention allows screening of candidate compounds for their ability to competitively bind and thus inhibit target enzyme, either for individual enzymes or members of a class of enzymes. The methodology avoids the use of substrates and identification of products for the target enzyme, by using a complementation assay with a distinct, but functionally linked, indicator enzyme. The enzyme complementation assay is sensitive to competitive binding of the target enzyme to a known inhibitor and a candidate inhibitor compound.

The assay relies on forming an active complex of the indicator enzyme, with the active complex being formed from a conjugate of an enzyme donor and a known inhibitor of the target enzyme, the "ED-conjugate," and an enzyme acceptor, "EA".

The rate and/or extent of formation of the active indicator-enzyme complex, or the activity of the complex, is affected by the binding of the target enzyme protein to the ED-conjugate.

The effect of the binding of the target enzyme to the ED-conjugate is measured by the rate and/or extent of substrate turnover by the indicator enzyme in the assay medium.

The subject invention finds particular application with enzymes as the target protein. The subject invention finds complementary application with those enzymes having substrates that are difficult to synthesize or expensive, and/or products that are difficult to detect. By employing the subject reagents, one can substitute the detection of product of the target enzyme with the detection of product of an indicator enzyme, such as β-galactosidase, where the products are readily detectable and the medium does not interfere with the sensitive detection of the product.

As a result, the subject invention provides efficient assay systems for identifying new inhibitors with increased affinity, and/or greater specificity.

Furthermore, the subject invention may use a single ED-conjugate carrying a known inhibitor of low specificity, in distinct library screens of candidate compounds, to identify plural high specificity inhibitors that specifically bind distinct targets of the low specificity inhibitor. The new inhibitors may act as lead compounds for effective drugs with increased potency and fewer side effects, for treating human disease and improving human health.

Further aspects of the invention are described in the following sections: (I) target enzymes, (II) inhibitors, (III) candidate compounds, (IV) enzyme portions for complementation, (V) enzyme complementation assays, (VI) β-galactosidase complementation assays, and (VII) examples.

I. Target Enzymes

The invention provides assay systems for identifying inhibitors of target enzymes. Target enzymes generally comprise any biologically produced material, or synthetic version or derivative thereof, that lowers the activation energy of a chemical reaction. Target enzymes typically are proteins or oligopeptides, but also may include or be nucleic acids, carbohydrates, lipids, or other biomolecules. The target enzymes of interest may be members from any of the major or minor classes of enzymes, including hydrolases, oxidoreductases, lyases, transferases, ligases, and isomerases, among others. Thus, target enzymes may include kinases, phosphatases, carboxylases, phosphodiesterases, dehydrogenases, oxidases, peroxidases, metalloproteinases, proteases, saccharidases, nucleases, reverse transcriptases, polymerases, recombinases, isomerases, helicases, gyrases, etc.

Each target enzyme functions in the assay by altering the ability of the ED-conjugate to complement indicator-enzyme activity. Thus, an ED-conjugate bound to the target enzyme will complement differently than an unbound (or distinctly bound) ED-conjugate, either producing more or less indicator-enzyme activity, based on size, charge, hydrophobicity, or any other physical or chemical property of the target enzyme. Generally, the target enzymes will be large enough that, when bound to the ED-conjugate, the rate and/or extent of formation of the fully active indicator-enzyme complex will be reduced, with concomitant reduction in the rate of product production.

The target enzyme may be obtained from any source. The target enzyme may be substantially pure, with purity greater than about 90%, may be a mixture of enzymes of the same or different classification; may share the same coenzyme; and/or may be a fraction from a naturally occurring source, e.g., cells, tissue, biological fluids (such as blood, saliva, urine, etc.), tissues biopsies, soil, water, etc. The target enzyme may be included in a sample supplied by a crude lysate, a lysate that has been fractionated or enriched for particular components, or the like. Enrichment may be achieved using chromatography, electrophoresis, density gradients, affinity columns, etc. The particular source of the target enzyme generally is not critical to this invention, since the selected reagents may be robust, and diverse components may be present without interference with the assay. Components that change the binding affinity of the target enzyme (s) which would interfere with the assay may be removed prior to performing the assay.

Target enzymes may be selected based on known or predicted functional importance to an organism's growth, survival, health, availability of known inhibitors, and/or importance to a particular disease state. In addition, targets enzymes may be selected based on structural similarity or distinctiveness between non-human and human homologs, uniqueness to a class or type of organism, and/or properties of mutants, among others. The selection of target enzymes to identify new antibiotics is described in Section II.C below.

The ability of a target enzyme to function in the assay relies on target-enzyme binding to ED-conjugate and test compounds. Thus, in some cases the target enzyme may be inactive catalytically, but still function effectively for binding to known and candidate inhibitors. For example, in some embodiments, the target enzyme may be used effectively in the assay even though it lacks a catalytically-required cofactor or constituent subunit, an activating covalent modification, and/or a compatible buffer milieu.

II. Inhibitors

Assays of the subject invention rely on a known target enzyme inhibitor, conjugated to an enzyme donor, to identify new inhibitors of the target enzyme. Inhibitors generally comprise any agent that specifically reduces the ability of a target enzyme to catalyze conversion of a substrate to product. An inhibitor generally binds to a target enzyme with a high affinity, having a binding constant of less than about $10^{-5}$ M, less than about $10^{-6}$ M, less than about $10^{-8}$ M, or even lower. Furthermore, an inhibitor may not act as a substrate, may act as an inefficient substrate, may be incompletely converted to a product, and/or may form a product that remains tightly bound to the target enzyme.

A. Inhibitor Mode of Action and Specificity

Known and candidate inhibitors bind competitively to a target enzyme, that is, these inhibitors may bind to a single common site, overlapping sites, or distinct, but mutually exclusive, binding sites. Thus, known and candidate inhibitors may compete for binding by directly occluding an inhibitor binding site or by indirectly altering a binding site, for example, by an allosteric mechanism.

Known and/or candidate inhibitors may bind reversibly to the target enzyme. Reversibly bound inhibitors may achieve a generally stable, equilibrium distribution of bound and unbound inhibitor, based on, at least partially, the on- and off-rates for target enzyme interaction.

Known and/or candidate inhibitors also may bind irreversibly to the target enzyme. Irreversibly bound inhibitors become covalently linked to the target enzyme, forming a long-lived covalent enzyme-inhibitor complex. Such irreversibly bound inhibitors are also referred to as suicide, activity-based, or mechanism-based inhibitors. These suicide inhibitors are often relatively unreactive chemically until bound to an active target enzyme, thus the term "activity-based". Furthermore, these suicide inhibitors may become frozen in a transition state complex that cannot be readily hydrolyzed, thus the term "mechanism-based". Highly specific and broad-specificity suicide inhibitors are available for many enzymes, as exemplified in the following U.S. Pat. No. 4,661,510, issued Apr. 28, 1998; U.S. Pat. No. 4,745,109, issued May 17, 1998; U.S. Pat. No. 5,567,597, issued Oct. 22, 1996; U.S. Pat. No. 5,714,361, issued Feb. 3, 1998; U.S. Pat. No. 5,786,462, issued Jul. 28, 1998; U.S. Pat. No. 5,942,631, issued Aug. 24, 1999; U.S. Pat. No. 5,962,442, issued Oct. 5, 1999; U.S. Pat. No. 6,008,386, issued Dec. 28, 1999; U.S. Pat. No. 6,121,007, issued Sep. 19, 2000; and U.S. Pat. No. 6,184,012, issued Feb. 6, 2001, incorporated herein by reference.

By linking a known inhibitor to an enzyme donor to provide an ED-conjugate, one can use the target enzyme as a binding partner to change the profile of activity of the indicator enzyme formed by the ED-conjugate complexing with an enzyme acceptor. In general, the greater the inhibition coefficient of a candidate compound, the more effectively it will compete with the known inhibitor for binding to the target enzyme. As a result, less of the target enzyme will be bound to the ED-conjugate, and the target enzyme will exert a smaller effect on indicator-enzyme activity.

For enzyme targets, there frequently are numerous known inhibitors that are available or that can be synthesized, where the known inhibitors will have the desired binding affinity to the enzymes. In some instances, the known inhibitor will show high specificity for binding to a single target enzyme, or for multiple members of structurally similar genus or family of target enzymes. Where a single inhibitor is known to inhibit a family or group of enzymes, one can determine the effect of a candidate compound on the group of enzymes and then deconvolute to determine the inhibition as to each of the enzymes in the group.

In other instances, the known inhibitor will be less specific or relatively nonspecific for target enzymes, but have a high affinity for a target enzyme of interest, as defined above, to allow screening for new inhibitors. A lower specificity inhibitor may bind distinct target enzymes having less than about 25%, less than about 20%, or less than about 15% amino acid identity, when the distinct target enzymes are compared over their entire lengths after optimal sequence alignment.

Inhibitors with low specificity, conjugated to enzyme donors, may be used to identify inhibitors with high specificity. In this case, the target enzyme of interest may be present in the assay relatively free of other target enzymes. This approach may have particular advantage because a single ED-inhibitor conjugate with broad target specificity may be used to identify distinct inhibitors in distinct screens with distinct target enzymes.

Known inhibitors that are less specific may have high binding affinity for a structurally divergent class of enzymes or for representatives from multiple classes of enzymes. Representatives from the class or classes may share a common mechanism of action or a common binding motif. For example, the known inhibitor may bind a coenzyme site shared by a plurality of proteins, such as binding site for adenine triphosphate ("ATP"), guanine triphosphate ("GTP"), nicotine adenine dinucleotide or its phosphate or reduced form ("NAD (P) (H)"), flavin mononucleotide ("FMN"), pyridoxal, etc. Alternatively, the known inhibitor may bind structurally diverse and/or mechanistically unrelated target enzymes.

B. Inhibitor Conjugates

Inhibitor conjugates are formed by coupling a known inhibitor of a target enzyme to an enzyme donor. Coupling includes any stable linkage between the known inhibitor and the enzyme donor and is generally a covalent linkage.

Enzyme donors may be conjugated to known inhibitors using an approach based on the structure, reactivity, derivatization, and/or method of preparation of the enzyme donor and inhibitor. Generally, conjugation may be carried out by chemical coupling or chemical synthesis in vitro, enzymatic coupling in vitro, or biological coupling in a biological expression vehicle, such as a cell, tissue, virus, and the like. For example, the enzyme donor and inhibitor may be coupled during their synthesis, either chemically or biologically, particularly when the inhibitor is a peptide or polypeptide. Alternatively, the enzyme donor and inhibitor may be synthesized separately and then coupled. The enzyme donor may be derivatized by chemical or genetic means to include a reactive group that facilitates coupling with the inhibitor. In addition, a linking moiety of any suitable size and chemical structure may be disposed between the enzyme donor and the inhibitor to facilitate chemical coupling, alter binding characteristics of the enzyme donor and/or the inhibitor, and/or modify any other desired property of the enzyme donor or inhibitor.

Exemplary methods of forming enzyme-donor conjugates are illustrated further in Section IV.A below and in the patents and patent application listed in the Background, which are herein incorporated by reference.

C. Inhibitors as Antibiotics

The subject invention may be used to identify new inhibitors that function as new antibiotics that are antiviral, antibacterial, antifungal, antiprotozoan, and/or antiparasitic. The enzyme complementation assay may be carried out using a target enzyme derived from a pathogenic, parasitic, and/or otherwise harmful or undesirable organism. Such organisms may includes viruses, such as HIV, hepatitis virus, herpesvirus, HPV, influenza, and the like; bacteria, such as *S. aureus, C. perfringens, V. parahaemolyticus, S. typhimurium, B. anthracis, E. coli*, and so on; fungi, such as from those included in the genuses Candida, Coccidioides, Blastomyces, Histoplasma, Aspergillus, Zygomycetes, Fusarium and Trichosporon, among others; protozoans, such as Plasmodia *P. vivax, P. falciparum*, and *P. malariae*, etc., *G. lamblia, E. histolitica*, Cryptosporidium, and *N. fowleri*, among others; and multicellular human parasites, such as flatworms, liver flukes, and Leptospira.

The target enzyme may be purified directly from the organism, or produced synthetically, enzymatically, or in a biological expression vehicle based on the gene, RNA, or amino acid sequence of the target enzyme. The new antibiotics identified may affect replication, transcription, translation, cell wall biosynthesis, and other metabolic pathways, among others. Such new antibiotics may result from screens using known antibiotics conjugated to enzyme donors. Exemplary antibiotics target specific enzymes are fluoroquinolones which inhibit bacterial gyrase and topoisomerase IV; penicillins which inhibit bacterial transpeptidases; antiviral drugs which inhibit human immunodeficiency virus proteases; and nucleoside analogs and non-nucleoside drugs which inhibit viral reverse transcriptase.

Alternatively, the new antibiotics may result from screens using any known high or low specificity inhibitor. Any new inhibitors identified with a target enzyme of interest may be additionally screened in parallel or in a distinct screen for specificity relative to other target enzymes, particularly a human homolog of the target enzyme.

D. Kinase and Phosphatase Inhibitors

The subject invention may be used to identify new inhibitors for kinases or phosphatases. The presence or absence of phosphates at key sites on proteins, carbohydrates, lipids, and nucleic acids are of particular regulatory importance in controlling a wide variety of cellular processes, including growth control, cell division, signal transduction, cell metabolism, cell differentiation, and development. Thus, new inhibitors to specific kinases and phosphatases may be useful in modulating these cellular processes.

Kinase inhibitors that are specific or non-specific, naturally occurring or synthetic are available for a wide variety of kinases. As illustrative of different kinases and their inhibitors are the following: for cyclin dependent kinases (CDK), p15INK4b, SU9518 (Yamasaki, et al., *Circ. Res.*, 88:650–6 (2001)); PD0183812 (Fry, et al., *J. Biol. Chem.*, February 6 (2001)); p21(WAF1), p27(Kip1), Bak (Don, et al., *Mol. Pharmacol.*, 59:784–94 (2001)); flavopiridol (Senderowicz, *Leukemia*, 15:1–9 (2001)); for glycogen synthase kinases (GSK) SB-415286, SB216763 (Cross, et al., *J. Neurochem.*, 77:94–102(2001)); 3-anilino-4-arylmaleimide (Smith, et al., *Bioorg. Med. Chem. Lett.*, 11:635–9 (2001)); for BCR/ABL, CIS1 (Taichi, et al., *Exp. Hematol.*, 29:556–61 (2000)); AG957. AG490. STI571 (Sun, et al., *Blood*, 97:2008–15 (2001)); for MSK1 and MAPKAPK-2, cheilanthane sesterterpenoids (Buchanan, et al., *J. Natl. Prod.*, 64:300–3 (2001)); for C-SRC, 7-pyrrolidinyl- and 7-piperidinyl-5-arylpyrrolo-[2,3-d]-pyrimidines (Altmann, et al., *Bioorg. Med. Chem. Lett.*, 11:853–6 (2001)); for uridine kinase, nifedipine and nimodipine (Najarian and Traut, *Neuroinhib. Neurol. Repair*, 14:237–41 (2000)); for thymidine kinase, 2'-O-acyl/alkyl substituted arabinosyl nucleoside (Balzirinie, et al., *Biochem. Pharmacol.*, 61:727–32 (2001)); for p38MAP kinase, RPR200765A (Melay, et al., *Bioorg. Med. Chem. Lett.*, 9:537–54 (2001)); for PKC, PKC412 (Propper, et al., *J. Clin. Oncol.*, 19:1485–92 (2001)).

The other enzymes associated with phosphate transfer are the phosphatases, which remove phosphate, as contrasted with kinases that add phosphate to serine, threonine and tyrosine. A number of inhibitors have been reported for protein phosphatases, types-1 and 2. These include for protein phosphate inhibitors (Bibb, et al., *J. Biol. Chem.*, Jan. 29 (2001)); sulfonated aminothiazoles (Wipf, et al., *Bioorg. Med. Chem. Lett.*, 11:313–7 (2001)); inhibitor-4 (Shirato, et al., *Biochemistry*, 39:13848–55 (2000)); carboxy terminal region of Rb protein (Tamraken and Ludlow, *J. Biol. Chem.*, 275:27784–9 (2000)); I-2 (Yang, et al., *J. Biol. Chem.*, 275:22635–44 (2000)); clavosines A and B (McCready, et al., *J. Biol. Chem.*, 275:36125–31 (2000)); NIPP-1, tautomycin, microcystin-LR, calyculin and okadaic acid (Connor, et al., *J. Biol. Chem.*, 274:22366–72(1999)); for CDC-25A phosphatase, steroidal inhibitors (Deng, et al., *J. Med. Chem.*, 44:843–8 (2001)); for alkaline phosphatase, phosphonoacetic acid and mercaptomethyl phosphonic acid (Holtz, et al., *Protein Sci.*, 9:907–15 (2000)); protein tyrosine phosphatase, benzofuran and benzothiophene biphenyls (Malamas, et al., *J. Med. Chem.*, 43:1293–310 (2000)); modified 2-oxalylaminobenzoic acid (Iversen, et al., *J. Biol. Chem.*, 275:10300–7 (2000)); for calcineurin phosphatase, calcineurin B homologous protein (Lin, et al., *J. Biol. Chem.*, 274:36125–31(1999)).

III. Candidate Compounds

Candidate compounds are included in the enzyme complementation assays to measure their ability to compete with a known inhibitor for the target enzyme. Candidate compounds generally comprise any material with the potential to competitively bind the target enzyme.

The candidate compound may be naturally occurring, synthetic, a component of a mixture, a member or mixture of members of a combinatorial library, and the like. The candidate compound will normally be an organic compound, including metalloorganic compounds, and may be aliphatic, aromatic, alicyclic, or heterocyclic or combination thereof, may be oligomeric, e.g. proteins, nucleic acids and polysaccharides, polar or non-polar, salts and neutral compounds, etc., and combinations thereof.

Candidate compounds will generally have a molecular weight of at least 125 and may be 50 kDal or more, particularly where the compound is oligomeric. In screens for small drugs, the candidate compounds will have a molecular weight generally in the range of about 125 to 2000 Dal, more usually not more than about 750 Dal. Candidate compounds will usually be composed of carbon, hydrogen, oxygen, nitrogen, sulfur, phosphorous, halogen, and may include metal atoms, particularly as ions.

IV. Enzyme Portions for Complementation

The subject invention relies on enzyme complementation to indirectly measure molecular interactions of interest. Enzyme complementation generally comprises formation of a complex between substantially inactive first and second portions of an indicator enzyme that substantially increases indicator enzyme activity. A substantial increase in activity is at least about 5-fold, about 20-fold, or about 100-fold.

Enzyme complementation may combine fully inactive enzyme portions to form an active enzyme, converting activity from undetectable to detectable. The first and second portions may have an inherent affinity for each other, where the inherent affinity is sufficient for measurable complex formation. Thus, the first and second portions may interact stably in a wild-type version or parent of the indicator enzyme and maintain this interaction capability as distinct, non-covalently linked portions. In this case, interacting foreign motifs fused to each portion may not be necessary to induce complex formation.

In some embodiments, interaction of the portions may change the multimerization state of one or both portions.

Multimerization state generally comprises the number of molecules of each portion associated before or after complex formation. For example, complex formation may convert the first and/or second portion from a monomer to a dimer, trimer, tetramer, or higher order multimer of either portion. Alternatively, complex formation may decrease the multimerization of a component. For example, the second portion may be an inactive homodimer that is converted to an active monomer by complex formation with the first portion.

The portions may be small and large enzyme fragments, respectively, as described below; may have any size relative to each other; may be overlapping or nonoverlapping regions of a parent enzyme; and/or may be derived from distinct, non-covalently linked subunits (or portions thereof) of a parental multi-subunit enzyme. The portions may include to wild-type or mutant amino acid sequences (insertions, substitutions, deletions, etc) relative to the parent indicator enzyme.

The first portion, generally referred to as the enzyme donor (ED), is fused to a known inhibitor of a target enzyme. The first portion may include a minor portion of the indicator enzyme, corresponding to less than about 40%, less than about 20%, or less than about 10% of the indicator enzyme, based on molecular weight of the indicator enzyme complex. Alternatively, or in addition, the first portion may include a minor portion of the wild-type or parental indicator enzyme, having less than about 40%, less than about 20%, or less than about 10% of the parental indicator enzyme, based on molecular weight of the parent.

The second portion, generally referred to as the enzyme acceptor (EA), may remain unfused. The second portion may include a major portion of the indicator enzyme, corresponding to greater than about 60%, greater than about 80%, or greater than about 90% of the indicator enzyme, based on molecular weight of the indicator enzyme complex. Alternatively, or in addition, the second portion may include a major portion of the wild-type or parental indicator enzyme, having greater than about 60%, greater than about 80%, or greater than about 90% of the indicator enzyme, based on molecular weight of the parent.

A. Preparation of ED-Conjugates

This section describes methods for preparing the enzyme donor-conjugate. In preparing the ED-conjugate, the target enzyme inhibitor will be selected in accordance with the target enzyme. Depending upon the nature of the known inhibitor, whether an oligopeptide, a nucleic acid, a polysaccharide, or a naturally occurring or synthetic, small organic compound in the range of about 125 Dal to 2 kDal, the method of synthesis may differ.

Where the known inhibitor is an oligomer that can be synthesized using an automatic apparatus, the compound may be synthesized on a solid support in accordance with conventional procedures. For oligopeptides, a nucleic acid-based coding sequence may be prepared and introduced into an expression vector for single celled organisms, e.g., bacteria and yeast, and the protein product worked-up in accordance with conventional procedures. For small (<2 kDal) naturally occurring or synthetic organic molecules, one will usually rely on the presence of a useful functional group or the introduction of a useful functional group.

The ED also may have an introduced functional group for coupling with the binding compound. These chemistries are amply described in the literature and will further be described below. For exemplary preparation methods of ED-conjugate and EA preparations see, for example, U.S. Pat. No. 5,643,734, incorporated herein by reference.

Enzyme-donors having a fused inhibitor domain can be prepared by the use of recombinant DNA techniques to improve the chemistry for coupling a known inhibitor. These enzyme-donor polypeptides provide convenient coupling sites for the covalent attachment of known inhibitor peptide at varying distances from the ED domain sequence required for complementation with EA.

As an example, enzyme-donor polypeptides of the type containing a polypeptide-coupling domain may be obtained from the alpha-region of β-galactosidase. The plasmid pUC13 may be cleaved at different sites in the alpha-region with a variety of enzymes, such as HaeII, BglI, MstI or PvuI to yield H-series, B-series, M-series and P-series alpha-regions respectively. The B- and H-series are treated with T4 DNA polymerase and S1 nuclease. The M-series and P-series are not treated. Each series of DNA is digested with SacI in the multiple cloning site and the small DNAs encoding an alpha-complementing peptide purified by agarose gel purification, electrophoresed onto DEAE-cellulose paper, eluted and ethanol precipitated.

Additionally, a plasmid may be genetically engineered to place the enzyme donor under regulatory control of a temperature inducible promoter. This may be accomplished using a λPr promoter in combination with a λrepressor protein (coded by the λCI gene) which is temperature sensitive, and allows for temperature induction of protein expression. The λ mutant gene, CI857 codes for a temperature sensitive repressor protein, which is inactive at temperatures greater than 37° C. Hereinafter, references to λCI gene refer to the CI857 mutant gene.

Alternatively, enzyme-donors having an inhibitor-coupling domain are prepared by the use of chemical polypeptide synthesis techniques to improve the chemistry for coupling inhibitor to the enzyme donor. These enzyme-donor polypeptides provide convenient coupling sites for the covalent attachment of inhibitor at varying distances from the portion of the enzyme donor required for complementation. Chemical peptide synthesis techniques may also be employed to prepare enzyme-donor conjugates comprising a complementation domain and an inhibitor domain. Enzyme-donor peptides may be synthesized on an automated peptide synthesizer by standard synthetic techniques. Briefly, a protected amino acid representing the carboxy-terminal amino acid of the inhibitor domain may be attached to cross-linked polystyrene beads. The resin beads function as a solid phase to which additional amino acids may be coupled in a step-wise manner. The peptide may be generated by growing the chain sequentially from the carboxy-terminus to the N-terminus. The solid phase facilitates driving the reaction rapidly to 100% completion by the use of excess reagents. The excess reagents can then be easily washed away. Upon completion of the synthetic steps, the peptide is removed from the resin and purified.

Enzyme-donor polypeptides prepared according to the methods of the present invention may have superior coupling chemistry for attachment to inhibitors, relative to conventional polypeptides, such as β-galactosidase-based CNBr2/M15, CNBr2/M112 and CNBr 24/X90 complementation systems. The enzyme-donor polypeptides prepared according to the present invention may be genetically engineered or chemically synthesized to provide sulfhydryl, amino or carboxyl groups appropriately positioned relative to the N-terminus so that analytes are covalently attached to these groups without interfering with the ability of the enzyme-donor conjugate to form catalytically active indicator enzyme by complexing with an enzyme-acceptor. Sulfhydryl and amino groups are preferred.

When a free sulfhydryl is present, it can react with a reactive group that is present on the known inhibitor. Such reactive groups include but are not limited to, reactive haloalkyl groups and acid/halo groups, p-mercuribenzoate groups and groups capable of Michael-type addition reactions including, for example, maleimides and groups of the type described in Mitral and Lawton, *J. Amer. Chem. Soc.*, 101:3097–3110 (1979). Haloalkyl as defined herein comprises any alkyl group from one to three carbon atoms substituted with bromine, iodine or chlorine. If the known inhibitor does not possess such reactive group for coupling to the free sulfhydryl of the enzyme-donor, a derivative of the known inhibitor can be prepared to contain such reactive group.

As another alternative, an ED-conjugate hybrid polypeptide may be prepared by ligating or fusing a gene encoding the enzyme donor with another gene encoding the known inhibitor (or a portion thereof). The expression of the ligated genes in an appropriate host cell results in a fusion protein product that is capable both of complementation with an enzyme-acceptor and specific binding to the target enzyme. Thus, fusion proteins prepared according to this embodiment of the present invention comprise two domains: (1) an enzyme donor domain, and (2) a protein domain, both encoded by a fused gene. As mentioned previously, the inhibitor protein domains utilized in this invention comprise sequences binding to the target enzyme.

In order to construct a gene encoding an ED-conjugate fusion protein, the two genes in question must be joined with their coding sequences such that the translational reading frame is maintained and is uninterrupted by termination signals. Further, if the host cell is a strain that contains a repressor, the fusion protein will be produced only in response to inactivation of the repressor of induction. In-frame, active fusion proteins may be identified by in vivo complementation of an enzyme-acceptor.

Fusion proteins may be constructed or expressed where the inhibitor polypeptide is attached to the—or C-terminus of the enzyme-donor polypeptide. A spacer sequence between the enzyme donor and the inhibitor polypeptide may be used to 1) enhance enzyme complementation, 2) limit the enzyme donor's effect on binding of inhibitor polypeptide to target enzyme, and/or 3) enhance the ability of an interaction between the target enzyme and inhibitor polypeptide to affect complementation, among others.

B. Preparing Enzyme Acceptors

Enzyme acceptors may be synthesized chemically, enzymatically, or in a biological expression vehicle, such as a cell or organism. Enzyme acceptors may be cleavage derivatives of full-length indicator enzyme, or may be produced de novo as a portion of the indicator enzyme. For example, enzyme acceptors may be expressed from nucleic acid expression vectors produced by recombinant DNA techniques. Enzyme acceptors may be highly purified, partially purified, or supplied as components of crude extracts.

Further details of enzyme acceptor preparation are included in Example 7 below, for β-galactosidase, and in the patents and patent applications which are incorporated by reference herein.

V. Enzyme Complementation Assays

This section describes methods for conducting enzyme complementation assays, including assay conditions and measuring results. Enzyme complementation assays may be conducted in vitro, in vivo, or a combination thereof.

A. Two-Stage Assays

The enzyme complementation assay may be divided into two stages, conducted serially, or at least partially in parallel:

1) a first incubation stage where the ED-conjugate competes with the candidate compound for the target enzyme, and 2) a second, indicator-enzyme assay stage, where substrate for the indicator enzyme is added and turnover determined. Thus, the first stage may include mixing the candidate compound, ED-conjugate, EA, and target enzyme, without the substrate, and incubating the mixture for a time sufficient for the candidate compound to compete with the ED-conjugate for binding to the target enzyme. However, the different components of the assay may be added simultaneously or consecutively. Usually, the candidate compound will be present before the ED-conjugate and EA are combined with the substrate, during the first stage. Any one of these three components may be added last, but preferably the candidate compound, target enzyme, and ED-conjugate are added together and incubated to allow for competitive binding of the candidate compound and the ED-conjugate to the target protein.

The duration of the first stage and the second stage will be selected to provide the necessary sensitivity for detection of the affinity of the candidate compound for the target enzyme. Generally, the total reaction time will be at least about one minute to about five minutes, and not more than about 4 hours. The duration of each of the two stages is based on at least several considerations, including: mechanism of inhibitor action, rate constants for binding and release of the components, and kinetics and sensitivity of detection for substrate conversion to product by the indicator enzyme.

The mechanism of inhibitor action, that is, the use of reversible or suicide inhibitors during the first stage, may determine the duration of the first stage. With reversible inhibitors, target enzymes may be combined with the inhibitor conjugate and candidate compound, and allowed to reach an approximate (or complete) equilibrium condition.

In this case, the first stage may be about five minutes, about fifteen minutes, and generally not more than about two hours. In contrast, with a suicide inhibitor as the known inhibitor, the duration of the first stage and the order of addition of the inhibitor conjugate and candidate compound may be more critical, because the indicator enzyme generally is assayed in a non-equilibrium association with inhibitor conjugate and an effective candidate compound. In this case, the duration of the first stage may be dependent upon the kinetics of suicide inhibitor linkage to the target enzyme and may be determined empirically. This duration may be sufficient to substantially complete reaction between the suicide inhibitor and the target enzyme in the absence of candidate compound, referred to as the time of reaction endpoint (tabs). Thus, effective candidate compounds will slow the rate of reaction between the suicide inhibitor and the target enzyme through competition for the target enzyme, and the reaction endpoint will be reached at a later time. As a result, a measurement at the same time of reaction endpoint ($t_{abs}$), but in the presence of an effective compound, will have more unreacted ED-conjugate and thus a different indicator enzyme activity.

Screens using suicide inhibitors may offer some advantages in the assay systems of the invention, by producing changes in the kinetics of enzyme complementation. Because suicide inhibitors react irreversibly with target enzymes, forming covalent bonds, the inhibitors may produce a greater dynamic range in the complementation assay relative to reversibly bound inhibitors. If target enzyme is present in sufficient excess over ED-conjugate, the ED-conjugate may be almost quantitatively converted to a form reacted with target enzyme, even though the suicide inhibitor may have only a moderate affinity for the target enzyme. This quantitative conversion may represent the maximum change in complementation achievable with that target enzyme, corresponding to a reversibly binding inhibitor conjugate with a very high binding affinity for target enzyme. However, kinetic inhibition of this quantitative conversion may be mediated by candidate inhibitors with moderate binding affinities, comparable to that of the suicide inhibitor. In contrast, a reversible inhibitor with very high binding affinity would be necessary to achieve a similar effect on enzyme complementation and thus effective competition would be achieved by a reversibly bound candidate compound with a comparable high binding affinity.

Prior to initiation of the second stage of the assay, an ED-conjugate that includes a suicide may be inactivated by a physical or chemical treatment/change in condition. The treatment or condition may include a change in temperature, pH, or ionic strength; removal or inactivation of cofactors or substrates, such as coenzymes, divalent cations, or metals; and/or introduction of an additional reactive partner for the suicide inhibitor, among others. Inactivation of the suicide inhibitor may at least substantially prevent any further reaction between the suicide inhibitor and the target enzyme. Such an inactivation of the suicide inhibitor allows the first stage to be substantially shorter than the second stage. This may be desirable when the suicide inhibitor reacts with target enzyme more quickly than the indicator enzyme reacts with its substrate.

The timing and duration of the second stage of the assay may be dependent upon the indicator enzyme's rate of substrate turnover, sensitivity of product or substrate detection, and type of inhibitors used. Generally, the length of the second stage should be sufficient for any active indicator enzyme to react with substrate to provide a detectable signal. The second stage may include measurement at a single time point or at multiple time points, producing a time course of activity. Measurements at multiple time points, where two or more time points form a time segment, indicate a rate of change of the signal, defined as enzyme activity. With a suicide inhibitor conjugated to ED, the enzyme activity may be measured during plural time segments, to determine a time-dependent change in enzyme activity within a single assay. In some embodiments, particularly with β-galactosidase as an indicator enzyme, the second stage may be about one minute or about five minutes, and generally not more than about one hour or, preferably, not more than about 0.5 hours.

B. Reaction Components

The concentration of the ED-conjugate, EA, and target enzyme will vary with the concentration range of interest of the candidate compound.

The concentrations of the candidate compound, ED-conjugate, EA, and target enzyme may be determined empirically to optimize the sensitivity of the assay for the particular target enzyme. Generally, the concentration of the ED-conjugate will be in the range of about 1 to 100, preferably about 2 to 25 times, the concentration of the candidate compound, and in those situations where the amount of candidate compound is unknown, times the average of the highest and lowest concentrations that can be estimated. The EA will be at least equal to the ED-conjugate and may be in substantial excess, usually not greater than about 10-fold excess. The equations for defining the concentrations are found in U.S. Pat. No. 4,378,428. The target enzyme concentration may be selected to optimize the change in indicator enzyme activity that would be produced by a candidate compound having the desired affinity. Generally, one would wish to see a change of at least about 10% in the turnover of the substrate during the course of the assay, preferably at least about 15%. Since in many cases, the target enzyme protein will have a relatively weak binding affinity, as compared to antibodies, the full dynamic range of the enzyme complex may not be achievable, except with suicide inhibitors (see above). Generally, at least about 20% of the full dynamic range will be sufficient for the assay, preferably at least about 35% and more preferably at least about 50%. ("Full dynamic range" is the range of indicator-enzyme activity produced in the absence of the target enzyme and at saturation of the ED-conjugate with the target enzyme.)

A substrate for the target enzyme may also be present. The substrate may be compound whose reaction is catalyzed or a coenzyme or both. Generally, a substrate may be included when the substrate binds to a site on the target enzyme that is distinct from an inhibitor binding site. For example, a serine-containing oligopeptide may be the substrate for a kinase, where the kinase would also bind ATP as a source of phosphate. The amount of substrate will usually be at least equal to $K_m$ and may be 2 to 10 times $K_m$.

Concentrations of the candidate compound may be as low as 1 pM and generally not more than about 0.1 mM, usually in the range of about 0.1 nM to 10 μM. Usually, there will only be one candidate compound in an assay, although mixtures may be used of up to about 10 different compounds, where rapid high-throughput screening is desired and positive results deconvoluted.

The incubation during the first stage will usually be carried out at a temperature in the range of about 15° C. to 50° C., more usually in the range of about 15° C. to 40° C., where the incubation may be temperature controlled. After sufficient time, the other components may be added to initiate the second stage and the temperature maintained at the incubation temperature or a different temperature in the same range for measuring indicator-enzyme activity.

The assay will normally be performed in an aqueous buffered medium selected for obtaining the desired binding affinity of the enzyme target(s) for the ED-conjugate. The pH of the medium will generally be in the range of about 3–11, more usually in the range of about 5–9. The volume of the assay composition is primarily one of convenience, taking into consideration the cost of the reagents, the available equipment, the number of assays to be performed, the sensitivity of detection, and the like. The assay may be performed in microtiter plate wells, ranging from 96 well plates to about 1536 well plates. The volumes may be from about 10 nL to 1 mL or from about 50 nL to 500 μL.

C. Measuring Indicator Enzyme Activity and Analyzing Results

The inhibitor affinity of a test compound is measured as a function of the activity of the indicator enzyme. Indicator activity is monitored by the appearance of a product of the enzymatically-catalyzed reaction or by disappearance of the enzyme substrate. This is the rate of conversion of substrate. A single point after initiation of the reaction or a plurality of points at different times may be taken. With suicide inhibitor-conjugates, the timing and duration of the indicator enzyme assay may be empirically determined to define a time point(s) at which the inhibitory effect of a reversible (or suicide) candidate compound would be measurable.

Substrate turnover may be monitored spectroscopically, electrochemically, or by any other suitable method. Spectroscopic methods generally involve interaction of electromagnetic radiation (light or wavelike particles) with matter, and may involve monitoring some property of the electromagnetic radiation that is changed due to the interaction. Exemplary spectroscopic methods include absorption, luminescence (including photoluminescence, chemiluminescence, and electrochemiluminescence), magnetic resonance (including nuclear and electron spin resonance), scattering (including light scattering, electron scattering, and neutron scattering), circular dichroism, diffraction, and optical rotation, among others. Exemplary photoluminescence methods include fluorescence intensity (FLINT), fluorescence polarization (FP), fluorescence resonance energy transfer (FRET), fluorescence lifetime (FLT), total internal reflection fluorescence (TIRF), fluorescence correlation spectroscopy (FCS), and fluorescence recovery after photobleaching (FRAP), their phosphorescence analogs, and bioluminescence resonance energy transfer (BRET), among others.

During the incubation stage, the reaction may be allowed to occur while measurements of other samples are performed. In this way, by appropriate staggering of the samples, the reader can be in relatively constant use, so that times between measurements of different samples can be very short. Large numbers of assays with different samples may be performed in microtiter well plates, so that incubation occurs simultaneously, reagents can be added simultaneously and the reading can be performed simultaneously. In addition, one or more wells may be used as controls, so that one has an immediate direct comparison between the samples and the controls.

Various controls can be employed. The controls may lack a candidate compound or have a known amount of a compound(s) of known inhibitor, so that indicator enzyme activity may be related to known compounds. By graphing the results with known amounts of compounds having known affinities, one can compare the results with the candidate compound. Where mixtures of target enzymes are involved, one can relate the average activity to the affinity of the compound. One may then deconvolute as to the individual target enzymes.

Additional controls may be assayed simultaneously in distinct wells, or sequentially. For example, unconjugated ED rather than an ED-conjugate may be tested. Furthermore, when the known inhibitor has a broad (low) specificity homologous target enzymes from distinct species may be assayed. For example, comparison of a bacterial target enzyme with its human counterpart may identify candidate antibiotics that are specific for the bacterial target as described above. Moreover, plural distinct target enzymes may be assayed separately to define the inhibitor specificity of a candidate compound.

D. In Vivo Assays

Assays may be conducted at least partially in vivo, generally in eukaryotic or prokaryotic cells. These assays may rely on in vivo expression of the ED-conjugate, enzyme acceptor, target enzyme, and/or candidate compounds. For example, each of these components of the assay may be expressed from nucleic acid expression vectors or from the cell's genome. In this case, the inhibitor and candidate compounds may be polypeptides and/or nucleic acids. Thus, the candidate compounds may be expressed from a nucleic-acid based expression library. This library may include cDNA, genomic DNA, synthetic DNA, RNA, or synthetic RNA, among others. Alternatively, some of the assay components may be introduced into cells by exposure of the cells to these components. Introduction of the components may be promoted by any suitable environmental or chemical treatment of the cells, such as, electroporation, lipofaction, or chemical permeabilization, among others.

Indicator enzyme activity resulting from in vivo complementation may be measured in cells or with lysates prepared from cells. When measured in cells, the cells may be living, dead, fixed, and/or permeabilized. Measurements in cells may include exposure of cells to chromogenic or fluorogenic substrates, among others. Measurements in lysates may be conducted as described above for the second stage of in vitro assays.

VI. β-Galactosidase Complementation Assays

Exemplary enzyme complementation assays to screen for enzyme inhibitors use β-galactosidase as an indicator enzyme. In these approaches, the first portion or ED, may include the alpha portion or the omega portion of β-galactosidase, among others. The second or EA portion may include a major remaining portion of β-galactosidase, which is overlapping or nonoverlapping with ED. Thus EA may include at least one-half of β-galactosidase that is absent from the first portion. The approaches for forming β-galactosidase ED-conjugates and enzyme acceptor may be generally suitable for forming other ED-conjugates and EA portions for other indicator enzymes. Further aspects of complementation assays using β-galactosidase, and suitable ED and EA portions, are described in the U.S. Pat. Nos. 4,708,927, 5,037,735, 5,362,625, 5,464,747, 5,604,091, and 5,643,734, which are incorporated by reference herein.

Substrates for β-galactosidase that may be suitable for spectroscopic analysis by absorbance and/or fluorescence include, but are not limited to: p-aminophenyl-β-D-galactopyranoside; 2'-N-(hexadecanol)-N-(amino-4'-nitrophenyl)-β-D-galactopyranoside; 4-methylumbelliferyl-β-D-galactopyranoside; napthyl-AS-B1-β-D-galactopyranoside; 1-napthyl-β-D-galactopyranoside; 2-napthyl-β-D-galactopyranoside monohydrate; O-nitrophenyl-β-D-galactopyranoside; -nitrophenyl-β-D-galactopyranoside; p-nitrophenyl-β-D-galactopyranoside; and phenyl-β-D-galacto-pyranoside, 5-bromo-4-chloro-3-indolyl-β-D-galactopyranoside, resorufin-β-D-galactopyranoside, 7-hydroxy-4-trifluoromethylcoumarin, ω-nitrostyryl-β-D-galactopyranoside, and fluorescein-β-D-galactopyranoside.

VII. EXAMPLES

The following examples describe selected aspects and embodiments of the invention, including methods for making and using staurosporine derivatives and ED-conjugates, experimental results with these materials in complementation assays, and methods for making enzyme acceptors. These examples are included for illustration and are not intended to limit or define the entire scope of the invention.

Example 1

Staurosporine Derivatives

Figure 3A:
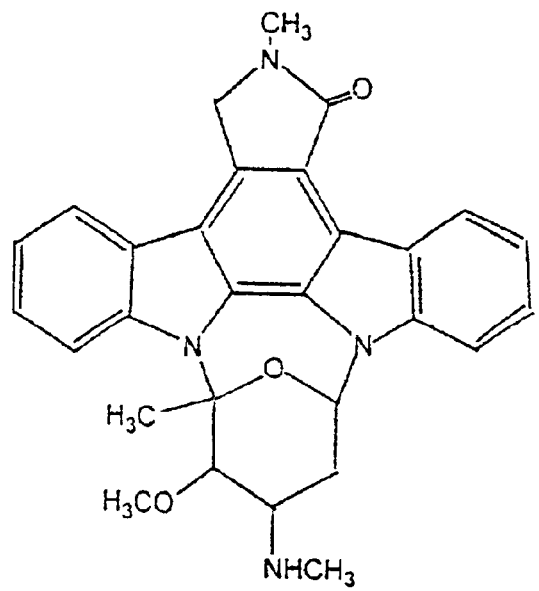
FIG. 3A is the structural formula for staurosporine.
Figure 3B:
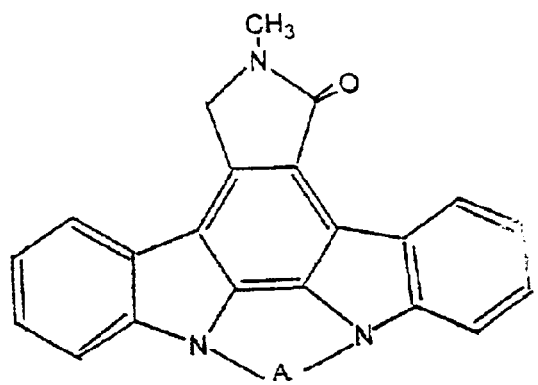
FIG. 3B is a formula comprising a portion of staurosporine wherein A on the heterocyclic ring corresponds to oxygen.
Figure 3C:
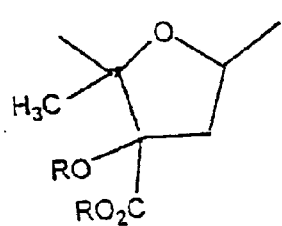
FIGS. 3C and 3D show different embodiments of "A".
Figure 3D:
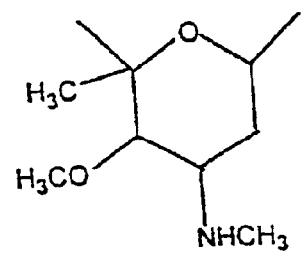

This example describes potential structures for staurosporine derivatives as seen in FIG. 3.

For different enzymes, different compounds will be attached to the ED to form the ED-conjugate. For serine/threonine kinases, compounds that can be used that have a binding affinity to the target enzymes of less than $10^{-6}$ M include staurosporine. Staurosporine has two hydrindane rings, where the para-annular carbon atom can conveniently serve as a site for functionalization. Alternatively, the nitrogen bonded to an annular carbon atom of the tetrahydropyran may be used for the site of attachment. The linking group will generally have from about 1 to 12 carbon atoms and from 1 to 4 heteroatoms in the chain, particularly oxygen, nitrogen and sulfur, where the linkage to the staurosporine may be an amide, thioether, ether, or ester, etc.

Derivatives of staurosporine can be prepared that retain their ability to bind to target kinases, while being labeled, so as to allow for detection of binding.

Staurosporine and derivatives thereof are depicted in FIG. 3, wherein R is alkyl or alkanoyl of from 1–3 carbon atoms, being alkyl when bonded to carboxy. Any one of the hydrogen atoms or any of the substituents on the furan or pyran rings may be substituted with a linking group, as described below, or may be removed from the ring. Particularly, the amino group present on the tetrahydropyran ring at position 4 is found to provide a site for linking that does not interfere with the binding of the staurosporine to the target kinase with high specificity and affinity, but also allows for conjugation to ED, where the ED can complex with the EA to form an active β-galactosidase, but also allows for modulation of the turnover rate of the β-galactosidase when the staurosporine conjugate is bound to the enzyme. By having a linking group from the amino group, one may also conjugate to ligands other than ED, since the binding affinity is retained.

For the most part, these compounds will have the following formula:

(deNHCH$_3$)STA-(NT)-R-L wherein
(deNHCH$_3$) STA is staurosporine without the methylamino group on the tetrahydropyran ring;
NH is amino;
T is NH or NCH$_3$;
R is a linking group having a chain of from 1 to 20, usually 4 to 16 atoms in the chain, where the chain is composed of C, N, O, S, P, and may be aliphatic, alicyclic, aromatic or heterocyclic, or combinations thereof, aliphatically saturated or unsaturated, particularly comprising aliphatic or heterocyclic groups;
R will generally have a total of from 1 to 40, usually 4 to 25 atoms other than hydrogen, particularly including C, N, O and S, where the heteroatoms will be present in from about 0 to 12, more usually from about 1 to 8, and will include the functionalities oxy, thio, carbonyl, both oxo- and non-oxo-carbonyl, amino, amido, phosphate, phosphonate, etc., where there may be from 0 to 12 heterofunctionalities, usually from about 2 to 10 heterofunctionalities wherein groups of particular interest include succinimido, thiosuccinimido, oxysuccinimido, amido, ethylenoxy and polyethyleneoxy of from 2 to 6, usually 2 to 4, ethyleneoxy groups, terminal monoaminoethyl- and diaminoethyl-polyethylenoxy of from 1 to 4 ethyleneoxy groups, ethylendiamino and polyethyleneamino of from 1 to 4 ethyleneamino groups, and the like;
L is a ligand of at least about 100 Dal and not more than about 5 kDal, usually not more than about 3 kDal, where the ligand may be a binding ligand, such as biotin, digoxin, 2,4-dinitrobenzene, or other molecule for which a naturally occurring binding protein is available or for which an antibody can be prepared; a molecule that directly provides for a detectable signal, such as a fluorescer, e.g. fluorescein, rhodamine, Cy3, Cy5, etc., chemiluminescer, electrochemical label, etc., or the ligand may be more than 5 kDal and be a particle, such as a carbon particle, latex particle, etc.

L is

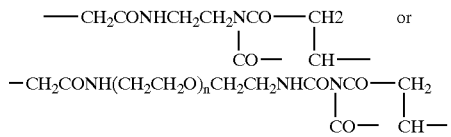

and n is 1 to 4.

The staurosporine conjugates are useful in a variety of assays, such as fluorescence polarization assays, spectrophotometric assays, electrochemical assays, etc.

Example 2

Staurosporine-CM-MEA

The title compound was prepared as follows:

A. Preparation of N-carboxymethylstaurosporine Methyl Ester

To a vial of staurosporine (0.5 mg, 1.07 μmole) was added dimethylformamide (250 ìL). An appropriately sized magnetic stirrer bar was added to the vial. To this were added methyl bromoacetate (4.8 mg, 31 μmole) and diisopropylethylamine (6.0 μL). Allowed the reaction mixture to stir overnight. High Performance Liquid Chromatography on a pharmaceutical C18 and a gradient of 0 (100% C) to 100% D (buffer C: 0.1% TFA in HPLC water and buffer D: 0.1% TFA in HPLC acetonitrile) analysis showed the reaction to be complete as one major product. N-carboxymethylstaurosporine, methyl ester was purified by HPLC, and electro-spray mass spectroscopy (ESI-MS) confirmed the identity of the product (M+1=539). Lyophilized the product fraction overnight. This was used in the next synthetic step.

B. Hydrolysis of N-carboxymethylstaurosporine, Methyl Ester

To the vial containing N-carboxymethylstaurosporine, methyl ester (~0.5–0.6 mg) was added HPLC grade methanol (250 μL) and HPLC grade water (250 μL). An appropriately sized magnetic stirrer bar was added to the reaction vial. To the reaction was added sodium hydroxide (1N, 100 μL). The reaction mixture was stirred overnight. Analysis of the reaction mixture by HPLC showed one major product peak. The product was isolated by HPLC, and confirmed by ESI-MS (M+1=525). Lyophilized the reaction mixture overnight. This amount was used for the next step synthesis.

C. Preparation of Amide of 2-(N-maleimidoethyl)amine and N-carboxymethylstaurosporine; Staurosporine-CM-MEA To the vial of N-carboxymethylstaurosporine (~0.5 mg, ~0.9 μmole) was added HPLC grade dimethylformamide (125 μL). To this was added HPLC grade DMSO (125 μL). An appropriately sized magnetic stirrer was added to the reaction vial. To the reaction mixture was added maleimidoethylamine HCl (1.1 mg, 6.2 μmole). Prepared HBTU-HOBT solution by dissolving 95 mg of O-benzotriazol-1-yl-N,N,N,N,tetramethyluronium hexafluorophosphate in 1 ml of a 0.5 M solution of 1-hydroxybenzotriazol hydrate in HPLC grade DMF. A solution of HBTU-HOBT (10 μL, ~5 μmole) was added to the reaction mixture. Placed the reaction on ice. Initiated the reaction by adding diisopropylethylamine (1.1 μL, ~6 μmole) to the reaction vial. Stirred the reaction for 5 min on ice. Analysis of the reaction mixture by HPLC showed a complete disappearance of the starting material. The product was purified by HPLC and confirmed by ESI-MS (M+1=647). The purified fraction was used directly in the conjugation.

Example 3

(Staurosporine-CM-MEA)$_2$-ED28

This example describes the preparation of the title compound, as follows:

A. Preparation of (Staurosporine-CM-MEA)$_2$-ED28 (ED28-STA)

To a desalted solution of ED28 (~0.25 mg, 26 nmole) in sodium phosphate buffer (0.160 mL) in an appropriately sized test tube was added a solution of purified staurosporine-CM-MEA from the previous example. Sodium phosphate buffer (100 mM, pH 8.5, 200–300 μL) was added to the reaction in order to adjust the pH to 7.0. Allowed the reaction to proceed for 1–2 hours. Purified the reaction mixture by HPLC (C4 protein column from Vydac, 1×25 cm, 5μ particles). A step gradient of 20% D (80% C) to 60% D was used in this purification. The conjugate elutes in 20 min at 4 mL/min flow rate. The conjugate was quantitated by UV-Vis spectroscopy, assuming $a_{280}$=86,000 $M^{-1}$ $cm^{-1}$ for this conjugate. The conjugate was confirmed by ESI-MS (M+1=11,082).

Example 4

Staurosporine-CM-MEA-ED4

This example describes the preparation of the title compound, as follows:

A. Preparation of Staurosporine-CM-MEA-ED4

To a solution of ED4 (0.2 mg, 2 nmole) in sodium phosphate buffer (0.230 mL) in an appropriately sized test tube was added a solution of purified and lyophilized staurosporine-CM-MEA (0.2 mg, 0.230 mL, 0.3 μmole) in HPLC grade acetonitrile from the previous step. Sodium phosphate buffer (100 mM, pH 8.5, 200–300 μL) was added to the reaction. The reaction was allowed to proceed for 1–2 hours. Purified the reaction mixture by HPLC (C4 protein column from Vydac, 1×25 cm, 5μ particles). A step gradient of 20% D (80% C) to 60% D was used in this purification. The conjugate elutes in 18.9 min at 4 mL/min flow rate. The conjugate was quantitated by UV-Vis spectroscopy, assuming $a_{280}$=51,000 $M^{-1}$ $cm^{-1}$ for this conjugate. The conjugate was confirmed by ESI-MS (M+1=10,449).

Example 5

Staurosporine-CM-MADOO

This example describes the preparation of the title compound, as follows:

A. Mono-Protection of 1,8-diamino-3,6-dioxaoctane (DADOO)

In an appropriately sized round bottom flask was dissolved DADOO (20.38 g, 0.138 mole) in dichloromethane (500 mL). An appropriately sized magnetic stirrer was added to the reaction flask. Cooled the reaction flask to −40° C. A solution of di-tert-butyldicarbonate (5 g, 0.023 mole) in dichloromethane (200 mL) was added, dropwise, to the reaction in 2 hours. After complete addition a clear solution was obtained. The reaction was allowed to warm to temperature slowly, and let stand overnight. At this point, small amounts of a white precipitate were formed. Washed the reaction mixture with water (3×100 mL), sodium hydroxide (1N, 3×100 mL) and saturated sodium chloride (2×50 ml). Dried the organic phase over sodium sulfate overnight. Sodium sulfate was removed by vacuum filtration. The solvents were removed by rotary evaporation. The organic residue was dried under high vacuum for 2 hour. This gave 5.3 g of crude product, N-butoxycarbonyl-dioxaaminooctane, as oil. This gave a single spot by thin layer chromatography (ethyl acetate: methanol 1:1). The product spot was visualized by ninhydrin spray. The crude product was used in the next step without further purification.

C. Preparation of 1-butoxycarbamoyl-8-(N-maleimido)-3,6-dioxaoctane (N-boc-MADOO)

In an appropriately sized round bottom flask was added N-boc-DADOO (3 g, 0.012 mole). To this was added dioxane (50 mL). An appropriately sized magnetic bar was added to the reaction flask. The reaction flask was cooled with ice. Methoxycarbonylmaleimide (1.87 g, 0.012 mole) was added to the reaction flask. The reaction mixture was stirred on ice for 15 min. Saturated sodium bicarbonate (50 mL) was added to the reaction mixture. Stirred the reaction on ice for 30 min. The reaction mixture was extracted into ethyl acetate (300 mL). The organic layers were washed with water (3×300 mL) and brine (2×50 mL). Dried the organic layer on sodium sulfate overnight. The product was purified by flash column chromatography on silica gel. The solvent used was ethylacetate hexane (70:30 v/v). Appropriate fractions were pooled, and the solvent was removed by rotary evaporation. The oily product (0.95 g) was dried under high vacuum for several hours.

$^1$H and $^{13}$C NMR confirmed the product. $^1$H NMR (CDCl$_3$, δ ppm) 6.715 (s, 1H, maleimide), 5.033 (bs, 1H, NH), 3.489–3.758 (m, 6H CH$_2$O), 3.27–3.37 (m, 2H, CH2N), 1.447 (s, 9H, CH$_3$). $^{13}$C NMR (CDCl$_3$, δ ppm), 170.6, 155.9, 134.14, 79.16, 77.21, 70.26, 69.91, 67.82, 40.38, 37.04 and 28.40.

C. Preparation of (Staurosporine-CM-MADOO)$_2$-ED28

Following the procedure for the preparation of staurosporine-CM-MEA$_2$-ED28, replacing the staurosporine-CM-MED with staurosporine-CM-MADOO, the title compound is prepared in the analogous way.

D. Preparation of Staurosporine-CM-MADOO-ED4

Following the procedure for the preparation of Staurosporine-CM-MADOO-ED4, replacing the staurosporine-CM-MEA with staurosporine-CM-MADOO, the title compound is prepared in the analogous way.

Example 6

Assay for Staurosporine

This example describes use of an β-galactosidase enzyme complementation assay to measure staurosporine.

Prepare serial dilutions of staurosporine (STA) or any other drug compound in assay buffer (ASB) containing 30 mM HEPES, pH=7.4, 10 mM MgCl$_2$, 0.4 mM EGTA, 20 mM NaCl, 0.01% Tween-20, 0.1% bovine beta-globuline. Pipette 10 μL of each dilution into 384-well plate. Do replicates. Prepare 36 μM peptide (substrate of a kinase) by diluting a stock solution (3.2 mM) with ASB.

Prepare 4× enzyme working solution (PKC). Prepare 0.25 nM ED$_{28}$-STA by diluted in 1 to 1 mix of ASB and enzyme donor dilution buffer (EDDB) containing 10 mM MES, pH=6.5, 200 mM NaCl, 10 mM EGTA, 2 mg/ml BSA fragments, 14.6 mM NaN$_3$. Mix equal amounts of a peptide, an enzyme working solution and ED-STA pipette 30 μL of peptide/PKC/ED$_{28}$-STA mix onto the plate containing 10 μL of staurosporine dilutions dispensed in each well. Tap the plate. Incubate 60 min at room temperature. Add 10 µL of 0.006 mg/ml enzyme acceptor (EA) diluted with Enzyme acceptor dilution buffer (EADB) containing 100 mM PIPES, pH=6.83, 400 mM NaCl, 10 mM EGTA, 0.005% Tween-20, 150 mM NaOH, 10 mM Mg acetate, 14.3 NaN$_3$. Add 15 µL of Galacton-Star/Emerald II (Chemiluminescent) substrate for β-galactosidase (Tropix). Incubate 10–15 min. Read chemiluminescence within the first hour after addition of EA reagent.

In a saturation binding study, ED$_{28}$-STA had affinity of 20 nM at PKC concentration of 20 nM. In a competition experiments staurosporine is shown to be able to displace ED$_{28}$-STA with a potency of 16 nM.

In additional studies, the potency of the staurosporine derivative (STA-CM) was assessed in separate assays (DiscoveRx STK HitHunter and Fluorescent Polarization STK Assays). IC$_{50}$ values for STA and STA—CM were 9 and 92 nM, respectively, (STK HitHunter Assay) and 22 and 220 nM (FP Assay).

The above results clearly show that the subject methods and compositions provide for a simple, rapid protocol that allows for the determination and screening of large numbers of compounds for their effect on the activity of a target enzyme. The reagents are readily prepared and are robust and not readily subject to interference. Enzymes are found to be able to bind to the ED-conjugate comprising an inhibitor for the enzyme and modify the enzymatic activity of the ED-EA complex over a wide dynamic range. The problems associated with many enzyme inhibitor assays are avoided. One does not need to provide a method of detecting the product, since a common substrate leading to a common product can be used for all of the enzyme inhibitors. The problems associated with enzymes involving the transfer of phosphate, namely kinases and phosphatases are avoided, since one does not need to have a different substrate for each enzyme and one does not need to have a different antibody for each product to perform immunoassays. The reagent, ED-conjugate is readily prepared, using fusion proteins, where the inhibitor is a polypeptide or synthesizing the reagent. Where the inhibitor is a small organic compound, various functionalities are available on the ED, so that by using the known inhibitors of the target enzyme protein and modifying them in known ways, useful ED-conjugates can be used.

Example 7

Preparation of β-Galactosidase Enzyme Acceptors

Illustrative techniques for the preparation of â-galactosidase enzyme-acceptors by deletion constructions are presented in detail below. These techniques may be adaptable to construction of enzyme acceptors derived from other indicator enzymes. Deletion construction techniques entail introduction of sites specific for particular restriction enzymes into the alpha-region of the β-galactosidase Z gene, followed by site-specific digestion, e.g., Ba131 digestion, to afford the desired amino acid sequence. After digestion with appropriate restriction enzymes, the viable enzyme-acceptors are isolated using in vivo complementation ability. For example, complementation can be screened by transforming plasmids, bearing thermoinducible genes coding for an enzyme-donor as well as the enzyme-acceptor of interest, into a strain such as AMA1004 (AMA1004 is galU, galK, StrA.sup.r, hsdR.sup.-, leuB6, trpC, .DELTA. (laCIPOZ) C29 (Casadaban et al., *Methods in Enzymology*, 100:293 (1983)) and selecting on plates containing the inducer isopropylthiogalactoside and the chromogenic substrate 5-bromo-4-chloro-3-indolyl-β-D-galactopyranoside. Colonies that are white at 30° C., but blue at 42° C., indicate creation of viable enzyme-acceptors. DNA from these enzyme-acceptors is cut with SalI, religated and transformed into AMA1004. The enzyme-acceptor polypeptides are then purified.

Alternatively, the enzyme-acceptors are prepared by direct synthesis of DNA using any commercial DNA synthesizer. The desired synthetic DNA sequence is then annealed and ligated into an appropriate plasmid vector. For example, plasmid p150 is digested with BamHI and XhoI restriction enzymes. The desired synthetic DNA sequence is then inserted into the BamHI/XhoI gap.

Alternatively, enzyme-acceptors of improved stability are prepared for use in enzyme complementation assays. The instability of enzyme-acceptors is effected most notably by oxidizing conditions. Ethylenediaminetetraacetic acid (EDTA) and reducing agents such as 2-mercaptoethanol or dithiothreitol dramatically improve the stability of enzyme-acceptors. These results point to exposed sulfhydryl groups on the enzyme-acceptors as the cause of instability. According to Jornvall, Fowler and Zabin (*Biochemistry*, 17: 5160–5164 (1978)) two of the 16 cysteine residues of the monomer polypeptide chain of native β-galactosidase are located on the surface of the enzyme. However, the enzyme-acceptor M15 contains 5 cysteine residues on the surface. Therefore, to improve enzyme-acceptor stability, the exposed cysteine residues are systematically removed from the improved enzyme-acceptors. The genes encoding the enzyme-acceptors are cloned into the appropriate M13 bacteriophage, single-stranded DNA isolated and annealed to appropriate oligonucleotide primers synthesized on the DNA synthesizer commercially available from Applied Biosystems, Inc. Standard methods as described by Zoller and Smith (*Methods in Enzymology*, 100, 468–500, Academic Press (1983)) are used in these constructions.

A series of in-frame sequence deletions of the β-galactosidase gene were constructed to prepare a series of enzyme-acceptors. pUC13 was digested with PvuII (yielding a blunt end) and ligated to an 8 bp synthetic DNA linker containing an XhoI restriction site to create a new plasmid, pUC13X. The alpha-region containing the XhoI restriction site was then replaced into the entire lacZ gene, which encodes native β-galactosidase without disrupting the remainder of the lacZ gene or the background plasmid. The Z gene contains two BglI sites. The first of these BglI sites is contained within the alpha-region in pUC13 downstream from the PvuII site where the XhoI linker was inserted. Thus the alpha-region from pUC13X was removed from the rest of the plasmid by digesting with BamHI and BglI and the 170 bp fragments designated B1X. The remainder of the lacZ gene which encodes β-galactosidase was obtained from the plasmid pβgal2 (Queen, *J. Mol. Appl. Genet.*, 2:1 (1983)). This plasmid was digested with BglI and EcoRI and two DNA fragments representing 93% of the Z gene were isolated. The terminus of each fragment was different from any other termini used in this construction. The isolated fragments were 2115 bp (hereinafter referred to as B2) and the 737 bp (hereinafter referred to as B3). The EcoRI restriction site in the Z gene is near the C-terminal end of the gene. This terminus must be present when the Z gene containing an XhoI site is constructed.

The mutant Z gene was inserted in pF29. Plasmid pF29 contains a Z gene s-region fused to the C-terminal end of the Z gene at the EcoRI site. This s-region is controlled by the λPr promoter inserted at a BamHI site. To construct pF29 two intermediate plasmids, pF15 and pF16 were constructed. pβgal2 was digested with AvaI and the cohesive 3' end filled in using the Klenow fragment and the four dNTPs to create blunt ends. A SalI linker (GGTCGACC) (New England BioLabs, Beverly, Mass.) was ligated to the linearized plasmid using T4 DNA ligase. The resultant DNA was digested with EcoRI and SalI, and a 300 bp DNA fragment representing the ω-end of the β-galactosidase Z-gene purified by agarose gel electrophoresis. This ω-region was fused to an.alpha-region under control of λPr as follows. pUC12 DNA (Bethesda Research Laboratories, Gaithersburg, Md.) was digested with BglI and blunt ends created by treatment with Klenow fragment and the four dNTPs. EcoRI linkers (GGAATTCC) (New England BioLabs, Beverly, Mass.) were ligated to the blunt ends with T4 DNA ligase. The DNA was digested with BamHI and EcoRI and a 180 bp fragment representing the alpha-region of the Z-gene was purified by agarose gel electrophoresis. The vector used to accept the alpha- and ω-gene fragments was pβgal2 digested with BamHI and SalI and purified by agarose gel electrophoresis to remove the lac operon sequences. The vector, alpha-gene and ω-gene fragments were ligated together using T4 DNA ligase. The unique ends of the DNA fragments direct the order in which these fragments were cloned. The product plasmid was designated pF15.

pF15 was further modified by converting the unique PvuII site into the vector SalI site using SalI linkers ligated to the blunt ends created by digesting pF15 with PvuII. This modified pF15 was then digested with BamHI and SalI, and the largest DNA fragment was purified by agarose gel electrophoresis which removes the α-ω-gene sequence and a DNA fragment located between the SalI site and the PvuII site. Unmodified pF15 was also digested with BamHI and SalI and the α-ω fragment purified. When the large fragment from the modified pF15 was ligated to the α-ω fragment, the plasmid pF16 was generated. pF16 is about 1350 base pairs smaller than pF15 and has the effect of moving a unique NdeI site much closer to the SalI site. This maneuver eliminates the unnecessary DNA sequences from being carried through subsequent constructions.

To construct pF29, pF16 was digested with ClaI and NdeI and the 1400 bp DNA fragment encoding the λCI, λPr, and the α- and ω-regions of β-galactosidase was purified by agarose gel electrophoresis. pUC13 was digested with AccI and NdeI and the vector was purified by agarose gel electrophoresis. Since the AccI and ClaI restriction sites have identical cohesive ends and the NdeI restriction sites share identical termini, ligation of the DNA insert from pF16 and the pUC13 vector can occur only in one orientation. Ligation with T4 DNA ligase yielded pF29. pF29 contains one EcoRI site and no ClaI sites which was desirable since a second EcoRI and the ClaI site would have interfered with the construction of modified plasmids (e.g., p149 and subsequent analysis of the deletion mutants created from p150 described below). pF29 was digested with BamHI and EcoRI, the intervening s-donor was removed and this vector was filled-in using B1X plus B2, plus B3 (B1X+B2+B3). The unique single-stranded end of each piece defines the order in which the pieces can be ligated together. The B1X, B2 and B3 were ligated into the pF29 vector digested with BamHI and EcoRI described above, thus reconstructing a Z gene with an XhoI linker at bp 102 encoding amino acid 34 under λPr control. The resultant plasmid was designated p149.

To create a method for screening for the creation of viable enzyme-acceptors following digesting with XhoI and Bal 31 digestion, a separate s-donor without the XhoI site was inserted into p149. An FnuDII digestion fragment from pUC13 containing the lacZ operator, promoter and alpha-donor was inserted into the SalI site of p149 which had been filled in with Klenow fragment. The resultant plasmid was designated p150. Deletions were created by digesting p150 with XhoI and then digesting the DNA with Bal 31 exonuclease. After Bal 31 treatment, the plasmid was ligated with T4 DNA ligase and transformed into AMA1004 host cells (AMA1004 is galU, galK, strA.sup.r, hsdR.sup., leuB6, trpC 9830, .DELTA.(lacIPOZ) C29, (Casadaban et al., Methods in Enzymology, 100:293 (1983)), and screened on Luria-Bertani plates containing the inducer isopropyl-thiogalactoside (IPTG) and the chromogenic substrate 5-bromo-4-chloro-3-indolyl-β-D-galactopyranoside (Xgal, Sigma Chemical Co., St. Louis, Mo.). Colonies that were white at 30° C., but blue at 42° C., indicated creation of viable enzyme-acceptors. Colonies were selected and plasmid DNAs prepared. Plasmid DNAs were digested with SalI, to remove the alpha-donor, religated and transformed into AMA1004 host cells. The sequence deletions were confirmed by Maxam and Gilbert sequencing and the enzyme-acceptor proteins purified.

Enzyme-acceptors have been constructed utilizing DNA synthesis techniques. For example, enzyme-acceptor 1 (EA1) was constructed from p149 except that the alpha-region which contains the XhoI linker was replaced with the following synthesized DNA fragments (5' to 3'):

```
(1) CAACAGTTGC GCAGCCTGAA                                  (SEQ ID NO: 1)

(2) AGGCTGCGCA ACTGTTGGGA AGGGCGATCG                       (SEQ ID NO: 2)

(3) ACCCAACTTA ATACCGATCG CCCTTCC                          (SEQ ID NO: 3)

(4) GTATAAAGTT GGGTAACGCC AGGGCCTTCC CA                    (SEQ ID NO: 4)

(5) CAACGTCGTG ACTGGGAAGG CCCTGGCGTT                       (SEQ ID NO: 5)

(6) GTCACGACGT TGTAAAACGA CGGCCAGTGA ATTCGAGCTC GCCCGGG    (SEQ ID NO: 6)

(7) GATCCCCGGG CGAGCTCGAA TTCACTGGCC GTCGTTTTA             (SEQ ID NO: 7)
```

These fragments encode an in-frame deletion of amino acids 26–43 of the lac Z gene and carry BamHI and BglI sticky ends. These fragments were annealed, purified by gel electrophoresis, treated with BamHI and ligated to B2 plus B3 and the pF29 vector. A positive colony was selected and confirmed by DNA sequence analysis.

All publications and patent applications referenced in the specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed:

1. A method for screening a candidate compound for effective inhibition of a target enzyme, employing as reagents:
   (1) an enzyme donor (ED)-conjugate comprising a substantially inactive first portion of an indicator enzyme conjugated to a known inhibitor of the target enzyme;
   (2) an enzyme acceptor (EA) comprising a substantially inactive second portion of the indicator enzyme, wherein a complex of the ED-conjugate and the EA forms an active indicator enzyme; and
   (3) a substrate for the indicator enzyme, wherein the substrate reacts to form a product, wherein at least one of the substrate and the product provides a detectable signal, the method comprising steps:
     a) combining the candidate compound, ED-conjugate, EA, target enzyme, and substrate under binding conditions, wherein the candidate compound and the ED-conjugate compete for the target enzyme; and
     b) determining the signal from at least one of the substrate and the product, whereby a difference in the signal observed in the absence of the candidate compound indicates that the candidate compound inhibits the target enzyme.

2. The method of claim 1, wherein the first and second portions of the indicator enzyme have an inherent affinity for each other that is sufficient to form the complex under the binding conditions.

3. The method of claim 1, wherein the first portion includes less than 20% of the indicator enzyme, based on molecular weight.

4. The method of claim 1, wherein the second portion includes at least 80% of the indicator enzyme, based on molecular weight.

5. The method of claim 1, wherein formation of the complex alters multimerization of at least one of the first and second portions.

6. The method of claim 1, wherein the indicator enzyme at least substantially corresponds to β-galactosidase.

7. The method of claim 6, wherein the first portion at least substantially includes the alpha portion of β-galactosidase.

8. The method of claim 1, wherein the target enzyme includes plural target enzymes.

9. The method of claim 1, wherein the target enzyme is derived from an organism selected from the group consisting of viruses, bacteria, fungi, protozoans, and multicellular human parasites.

10. The method of claim 1, wherein the target enzyme is selected from the group consisting of hydrolases, oxidoreductases, lyases, transferases, ligases, and isomerases.

11. The method of claim 1, wherein the target enzyme includes a kinase.

12. The method of claim 1, wherein the inhibitor is known to specifically bind distinct target enzymes, the distinct target enzymes having less than 25% amino acid identity.

13. The method of claim 1, wherein the known inhibitor is a suicide inhibitor.

14. The method of claim 1, wherein the combining comprises as a first step of mixing the candidate compound, ED-conjugate, EA, and target enzyme and incubating the mixture for sufficient time for the candidate compound to compete with the ED-conjugate for binding to the target enzyme; said first step followed by a second step of adding the indicator enzyme substrate and incubating for sufficient length of time for any active indicator enzyme formed to react with the substrate to provide the signal.

15. The method of claim 14, wherein the inhibitor is a suicide inhibitor, and the first step has a duration sufficient to at least substantially complete reaction between the suicide inhibitor and the target enzyme in the absence of candidate compound.

16. The method of claim 14, wherein the inhibitor is a suicide inhibitor that reacts with the target enzyme, and any further reaction of the suicide inhibitor with the target enzyme is at least substantially prevented before initiating the second step.

17. The method of claim 1, wherein combining is at least partially carried out in cells.

18. The method of claim 1, wherein determining step includes detecting any change in the signal in the presence and absence of the candidate compound at a time point.

19. The method of claim 1, wherein rate of change in the signal defines enzyme activity, and determining step includes detecting enzyme activity in the presence and absence of the candidate compound.

20. The method of claim 1, wherein the known inhibitor is a suicide inhibitor that reacts with the target enzyme in the absence of candidate compound until a time of reaction endpoint, and determining step includes detecting any change in the signal in the presence and absence of the candidate compound at approximately the time of reaction endpoint.

21. A method for screening a candidate compound for effective inhibition of a target enzyme, employing as reagents:
(1) an ED-conjugate comprising a substantially inactive first portion of β-galactosidase conjugated to an inhibitor of the target enzyme;
(2) an enzyme acceptor (EA) comprising a substantially inactive second portion of β-galactosidase, whereby the ED-conjugate and the EA complex to form an active â-galactosidase; and
(3) a substrate for the β-galactosidase, wherein the substrate reacts to form a product, and at least one of the substrate and product provides a detectable signal, the method comprising steps:
  a) combining the candidate compound, ED-conjugate, EA, target enzyme, and β-galactosidase substrate under binding conditions, wherein the candidate compound and the ED-conjugate compete for the target enzyme; and
  b) determining the signal from at least one of the substrate and product, whereby a difference in the signal observed in the absence of the candidate compound indicates the candidate compound inhibits the target enzyme.

22. The method of claim 21, wherein the first portion includes less than 20% of β-galactosidase, based on molecular weight.

23. The method of claim 21, wherein the first portion at least substantially includes at least one of the alpha portion and the omega portion of β-galactosidase.

24. The method of claim 21, wherein the second portion includes at least 80% of β-galactosidase, based on molecular weight.

25. The method of claim 21, wherein the second portion includes at least one-half of β-galactosidase sequences that are absent from the first portion.

26. The method of claim 21, wherein the target enzyme includes a kinase.

27. The method of claim 21, wherein the target enzyme includes plural target enzymes.

28. The method of claim 21, wherein the target enzyme in selected from the group consisting of hydrolases, oxidoreductases, lyases, transferases, ligases, and isomerases.

29. The method of claim 21, wherein the inhibitor is known to specifically bind distinct target enzymes, the distinct target enzymes having less than 20% amino acid identity.

30. The method of claim 21, wherein the inhibitor is a suicide inhibitor.

31. The method of claim 21, wherein the target enzyme is at least substantially inactive in its ability to turnover substrate.

32. A method for screening a candidate compound for effective inhibition of at least one target kinase, employing as reagents:
(1) an ED-conjugate comprising the alpha-portion of β-galactosidase conjugated to an inhibitor of the at least one kinase;
(2) an enzyme acceptor (EA) comprising at least a major portion of the remaining portion of â-galactosidase, whereby when the ED-conjugate and the EA complex an active β-galactosidase is formed; and
(3) a substrate for the β-galactosidase, wherein the substrate reacts to form a product, and at least one of the substrate and the product provides a detectable signal, the method comprising steps:
  a) combining the candidate compound, ED-conjugate, EA, at least one target kinase and β-galactosidase substrate under binding conditions, wherein the candidate compound and the ED-conjugate compete for the at least one target kinase; and
  b) determining the signal from at least one of substrate and product, whereby a difference in signal observed in the absence of the candidate compound indicates the candidate compound inhibits the at least one kinase.

33. The method of claim 32, wherein substrate for at least one kinase is combined in the combining step.

34. The method of claim 32, wherein the combining comprises a first step of mixing the candidate compound, ED-conjugate, EA, and at least one target kinase and incubating the mixture for sufficient time for the candidate compound to compete with the ED-conjugate for binding to the at least one the kinase; followed by adding the β-galactosidase substrate and incubating for sufficient time for any complex formed to react with the β-galactosidase substrate to provide a detectable signal.

35. The method of claim 34, wherein the kinase substrate is an oligopeptide.

36. The method of claim 32, comprising a plurality of kinases.

37. The method of claim 32, wherein the at least one kinase is obtained from a cellular lysate.

38. A method for screening a candidate compound for effective inhibition of at least one target kinase, employing as reagents:
(1) an ED-staurosporine conjugate comprising the alpha-portion of β-galactosidase;
(2) an enzyme acceptor (EA) comprising at least a major portion of the remaining portion of β-galactosidase, whereby when the ED-conjugate and the EA complex an active β-galactosidase is formed; and
(3) a substrate for the β-galactosidase, wherein the substrate reacts to form a product, and at least one of the substrate and the product provides a detectable signal, the method comprising steps:
  a) incubating the candidate compound, ED-staurosporine conjugate, EA, and at least one target kinase under binding conditions, wherein the candidate compound and the ED-staurosporine conjugate compete for at least one target kinase;
  b) adding substrate for the β-galactosidase; and
  c) determining the signal from at least one of the substrate and product, whereby a difference in the signal observed in the absence of the candidate compound indicates the candidate compound inhibits the at least one kinase.

39. The method of claim 38, wherein the at least one kinase is phosphokinase C.

40. The method of claim 39, wherein substrate for phosphokinase C is added in the incubating step.

41. The method of claim 38, wherein the substrate for the β-galactosidase produces a fluorescent product.

42. A method for high throughput screening of candidate compounds for effective inhibition of at least one target kinase, employing as reagents:
(1) an ED-conjugate comprising the alpha-portion of β-galactosidase conjugated to an inhibitor of the at least one kinase;
(2) an enzyme acceptor (EA) comprising at least a major portion of the remaining portion of β-galactosidase, whereby when the ED-conjugate and the EA complex an active β-galactosidase is formed; and (3) a substrate for the β-galactosidase, wherein the substrate reacts to form a product, and at least one of the substrate and the product provides a detectable signal, the method comprising steps:
  a) combining in separate wells of a microtiter well plate different ones of the candidate compounds, ED-conjugate, EA, at least one target kinase, and β-galactosidase substrate under binding conditions, wherein the candidate compound and the ED-conjugate compete for at least one target kinase; and
  b) determining the signal from at least one of the substrate and product in each of the wells, whereby a difference in signal observed in the absence of the candidate compound indicates the candidate compound inhibits the at least one kinase.

43. The method of claim 42, wherein the microtiter well plate comprises at least 96 wells.

44. The method of claim 43, wherein substrate for at least one kinase is included in each of the wells.

45. The method of claim 42, wherein at least one well lacks a candidate compound.

46. The method of claim 42, wherein the β-galactosidase substrate produces a fluorescent product and the determining is with a microtiter well plate fluorimeter.

47. A compound of the formula:

(deNHCH$_3$)STA-(NH)-R-L wherein (deNHCH$_3$)STA is staurosporine without the methylamino group on the tetrahydropyran ring;

wherein NH is amino; R is a linking group having a chain of from 1 to 20, wherein the chain is composed of C, N, O, S, P, and is aliphatic, alicyclic, aromatic or heterocyclic, or combinations thereof and wherein L is a particle or a ligand of at least about 100 Dal and not more than about 5 kDal.

48. The compound of claim 47, wherein L is a chain comprising at least one succinimido group, an amido group, and from 1 to 4 alkyleneoxy groups.

49. The compound of claim 47, wherein L is

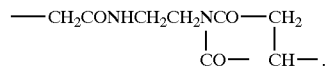

50. The compound of claim 47, wherein L is

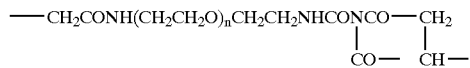

and n is 1 to 4.

51. A compound of the formula

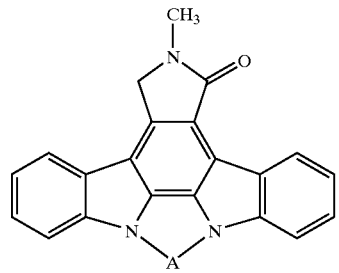

wherein A is

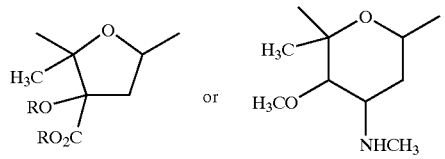

wherein R is a linking group having a chain of from 1 to 20 atoms in the chain, wherein said chain is composed of C, N, O, S, P and is aliphatic, alicyclic, aromatic or heterocyclic, or a combination thereof; and wherein any one hydrogen on the ring or a substituent on the ring is replaced with a bond or linking group to an enzyme donor from β-galactosidase.

* * * * *

SEQUENCE LISTING

```
<160> NUMBER OF SEQ ID NOS: 7

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
caacagttgc gcagcctgaa                                                    20

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
aggctgcgca actgttggga agggcgatcg                                         30

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
acccaactta ataccgatcg cccttcc                                            27

<210> SEQ ID NO 4
<211> LENGTH: 32
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
gtataaagtt gggtaacgcc agggccttcc ca                                      32

<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
caacgtcgtg actgggaagg ccctggcgtt                                         30

<210> SEQ ID NO 6
<211> LENGTH: 47
<212> TYPE: DNA
```

-continued

```
<213> ORGANISM: Artificial Sequence
<220> FEATURE:
<223> OTHER INFORMATION: Description of Artificial Sequence: Synthetic
      oligonucleotide

<400> SEQUENCE: 6
gtcacgacgt tgtaaaacga cggccagtga attcgagctc gcccggg                          47

<210> SEQ ID NO 7
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatccccggg cgagctcgaa ttcactggcc gtcgtttta                                   39
```